(12) United States Patent
Cone et al.

(10) Patent No.: US 10,921,842 B2
(45) Date of Patent: *Feb. 16, 2021

(54) PEDAL WITH SLIDING AND LOCKING MECHANISMS FOR SURGICAL ROBOTS

(71) Applicant: VERB SURGICAL INC., Mountain View, CA (US)

(72) Inventors: Taylor Cone, Belmont, CA (US); Joan Savall, Palo Alto, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/674,898

(22) Filed: Nov. 5, 2019

(65) Prior Publication Data

US 2020/0125131 A1 Apr. 23, 2020

Related U.S. Application Data

(63) Continuation of application No. 16/038,125, filed on Jul. 17, 2018, now Pat. No. 10,503,199.

(51) Int. Cl.
*G05G 1/405* (2008.04)
*A61B 34/00* (2016.01)
(Continued)

(52) U.S. Cl.
CPC ............. *G05G 1/405* (2013.01); *A61B 34/25* (2016.02); *A61B 34/35* (2016.02); *A61B 34/70* (2016.02); *A61B 34/76* (2016.02); *B25J 13/04* (2013.01); *G05G 1/44* (2013.01); *A61B 2017/00199* (2013.01); *A61B 2017/00212* (2013.01);
(Continued)

(58) Field of Classification Search
CPC G05G 1/30; G05G 1/40; G05G 1/405; G05G 1/42; G05G 1/44; G05G 1/445; B25J 13/04; A61B 2017/00973; A61B 34/25; A61B 34/35; A61B 34/70; A61B 34/76
See application file for complete search history.

(56) References Cited

U.S. PATENT DOCUMENTS

| | | | |
|---|---|---|---|
| 4,837,857 A | 6/1989 | Scheller et al. | |
| 4,965,417 A | 10/1990 | Massie | |

(Continued)

FOREIGN PATENT DOCUMENTS

| | | |
|---|---|---|
| CN | 107874834 A | 4/2018 |
| EP | 3085318 A1 | 10/2016 |
| WO | 20141205166 A1 | 12/2014 |

*Primary Examiner* — Prasad V Gokhale
(74) *Attorney, Agent, or Firm* — Womble Bond Dickinson (US) LLP

(57) ABSTRACT

A foot pedal system for controlling a surgical robotic system, the foot pedal system comprising a foot pedal assembly movably coupled to a foot pedal assembly platform. The foot pedal assembly having a foot pedal base, a foot pedal pivotally coupled to the foot pedal base, and a foot pedal platform, the foot pedal base operable to slide across the foot pedal platform along an x-axis and a y-axis to an arrangement of activation positions. The foot pedal platform operable to translate and rotate with respect to the foot pedal assembly platform to any position along the foot pedal assembly platform, and the foot pedal platform is operable to engage or disengage with the foot pedal assembly platform at the any position along the foot pedal assembly platform.

18 Claims, 14 Drawing Sheets

(51) Int. Cl.
*A61B 34/35* (2016.01)
*B25J 13/04* (2006.01)
*G05G 1/44* (2008.04)
*A61B 17/00* (2006.01)
*G05G 1/38* (2008.04)
*G05G 1/42* (2008.04)

(52) U.S. Cl.
CPC ............... *A61B 2017/00221* (2013.01); *A61B 2017/00973* (2013.01); *G05G 1/38* (2013.01); *G05G 1/42* (2013.01)

(56) References Cited

U.S. PATENT DOCUMENTS

| | | | |
|---|---|---|---|
| 5,422,521 A | 6/1995 | Neer et al. | |
| 5,583,407 A * | 12/1996 | Yamaguchi | G06F 3/0334 |
| | | | 318/551 |
| 5,635,777 A * | 6/1997 | Telymonde | H01H 3/14 |
| | | | 307/119 |
| 5,787,760 A * | 8/1998 | Thorlakson | G05G 1/30 |
| | | | 200/86.5 |
| 5,883,615 A | 3/1999 | Fago et al. | |
| 5,889,510 A | 3/1999 | Klarlund | |
| 6,600,477 B1 * | 7/2003 | Howell | G06F 3/0334 |
| | | | 345/156 |
| 7,877,171 B2 | 1/2011 | Gassner | |
| 7,977,171 B2 | 7/2011 | Yang et al. | |
| 8,340,863 B2 | 12/2012 | Karatsinides | |
| 9,301,811 B2 | 4/2016 | Goldberg et al. | |
| 9,375,288 B2 | 6/2016 | Robinson et al. | |
| 9,439,806 B2 | 9/2016 | Eastman et al. | |
| 10,368,955 B2 * | 8/2019 | Cone | G05G 1/445 |
| 10,503,199 B1 | 12/2019 | Cone et al. | |
| 2002/0107573 A1 | 8/2002 | Steinberg | |
| 2006/0219049 A1 | 10/2006 | Horvath et al. | |
| 2010/0198200 A1 | 8/2010 | Horvath | |
| 2013/0245834 A1 | 9/2013 | Laxhuber et al. | |
| 2014/0328469 A1 * | 11/2014 | Lee | G05G 1/30 |
| | | | 378/205 |
| 2015/0003898 A1 | 1/2015 | Shiozaki | |
| 2015/0029047 A1 * | 1/2015 | Levasseur | A63F 13/214 |
| | | | 341/21 |
| 2015/0038981 A1 | 2/2015 | Kilroy et al. | |
| 2015/0323953 A1 * | 11/2015 | Klestil | G05G 5/03 |
| | | | 74/470 |
| 2017/0007218 A1 * | 1/2017 | Lai | G05G 1/305 |
| 2018/0099608 A1 | 4/2018 | Salter et al. | |
| 2018/0280099 A1 * | 10/2018 | Cone | B25J 13/04 |
| 2019/0314005 A1 | 10/2019 | Ishihara et al. | |

* cited by examiner

PEDAL WITH SLIDING AND LOCKING MECHANISMS FOR SURGICAL ROBOTS

CROSS-REFERENCE TO RELATED APPLICATION

This application is a continuation of U.S. application Ser. No. 16/038,125, filed on Jul. 17, 2018.

FIELD

An embodiment of the invention relates to a pedal with sliding and locking mechanisms for surgical robotics. More specifically, embodiments of the invention relate to a multifunctional two-dimensional (2D) slider foot pedal assembly, and a selectively locking and repositionable foot pedal system. Other embodiments are also contemplated.

BACKGROUND

In a surgical robotic system, a robotic arm has a surgical tool attached to its distal end that is remotely operated by a surgeon. Applications include endoscopic surgery, which involves looking into a patient's body and performing surgery inside, for example the abdominal cavity, using endoscopes and other surgical tools that are attached to the ends of several robotic arms. The system gives the surgeon a close-up view of the surgery site, and also lets the surgeon operate the tool that is attached to the arm, all in real-time. The tool may be a gripper with jaws, a cutter, a video camera, or an energy emitter such as a laser used for coagulation. The tool is thus controlled in a precise manner with high dexterity in accordance with the surgeon manipulating a handheld controller. Some functions of the system such as control of the energy emitter may be assigned to a foot pedal controller that the surgeon manipulates with their foot.

SUMMARY

An embodiment of the invention is directed to a multifunctional two-dimensional ("2D") slider foot pedal assembly. The 2D slider foot pedal assembly may allow a user to activate at least four distinct robotic operations or functions using a single pedal. Representatively, the foot pedal assembly may include four activation positions that the user can select by sliding (e.g., translating and rotating) the pedal to the desired activation position. The activation positions are, in turn, mapped to desired functions that will execute when the user presses the pedal. To control the desired operation or function, the user activates the pedal (e.g., presses) once at the activation position. The foot pedal assembly therefore allows the user to access and activate multiple robotic operations or functions with just one foot and a single pedal, in some cases, without actually watching or otherwise viewing the position of the foot. The foot pedal assembly can minimize the risk of an unintentional activation of a pedal when moving between pedals, since the user controls all operations with a single pedal and without removing their foot from the pedal. Representatively, the foot pedal assembly may include a full-foot pedal coupled to a foot pedal base and a foot pedal platform. In one embodiment, the foot pedal may have a fulcrum (or axle) close to the heel of the user's foot, and which can be activated by the user rocking the foot forward, and in turn, rotating/pivoting the foot pedal relative to the foot pedal base. In some cases, the foot pedal may have multiple stages of activation depending on the desired function or operation to be controlled. In addition, in some cases, there may be an active feedback mechanism (e.g., vibration, force feedback, etc.) to give the user a haptic response, for example when the pedal is activated. Still further, the foot pedal may have a passive rotation about the heel (e.g., an axis going through the heel) to allow the user to comfortably angle their foot while maintaining contact with the foot pedal. The foot pedal base, to which the foot pedal is coupled, may be slidably position on the foot pedal platform. The foot pedal base may translate and rotate freely along a horizontal plane (e.g., planar contact surface) of the foot pedal platform between different activation positions. For example, in one embodiment, there may be an arrangement of four or five activation positions. Representatively, each corner of the foot pedal platform may have an activation position, for a total of four activation positions corresponding to at least four different robotic operations or functions. In addition, in some cases, there may be an additional activation position at the center of the foot pedal platform, for a total of five activation positions. This additional center activation position may correspond to a robotic operation or function when the pedal is pressed. In other cases, the center activation position may not correspond to a robotic operation or function, for example, may be a "clutch" position used to transition between operations or functions when the pedal is pressed. The foot pedal and/or foot pedal base may translate and rotate between the activation positions to control the desired robotic function. It is noted that in describing the foot pedal and/or foot pedal base (or any other components herein) as operable to translate "and" rotate between positions, it should be understood that this phrase is intended to mean the assembly can perform both translation and rotation operations, but not necessarily at the same time. Rather, these operations may occur sequentially or at the same time. For example, the foot pedal base may first translate in a particular direction, then rotate while moving from one activation position to another activation position (or while at a position), or may simultaneously translate and rotate while moving between positions.

The foot pedal assembly may further include a locking mechanism or assembly to secure, or otherwise hold, the foot pedal base (and foot pedal) at the desired activation position. For example, the locking mechanism or assembly may include an arrangement of platform magnets, one near each of the activation positions of the foot pedal platform (e.g., inside corners of the platform), and complimentary base magnets arranged on the foot pedal base to align with the platform magnets. For example, the platform magnets may be attached to inside corners of the sliding surface of the platform, and the base magnets may be attached to outside corners of the foot pedal base. During operation, the foot pedal base (and foot pedal) may "snap" to, or otherwise be secured, at the desired activation position by the magnetic forces between the magnet assemblies.

An embodiment of the invention is further directed to a foot pedal assembly positioning system that allows a user to place two foot pedals (one per foot) in a desired location and orientation and apply forces that lock them to a foot pedal assembly platform. The foot pedal assembly may be a rocking type foot pedal assembly as previous discussed, or could be any other type of foot pedal assembly (e.g., a floating foot pedal assembly). Regardless of the type of foot pedal assembly, the foot pedal assembly positioning system of this embodiment allows the user to keep their foot on the pedals (eliminating the need to locate pedals when activation is desired) while also enabling the user to change the foot pedal assembly location and/or orientation throughout a procedure or task. The system therefore addresses the ergonomic need to reposition the feet during a procedure, which sometimes arises. Representatively, in some cases, the foot pedal system may include a foot pedal assembly and a foot pedal assembly platform to which the assembly is slidably coupled. The foot pedal assembly platform may be (or otherwise include) a ferromagnetic plate that allows the foot pedal assembly to translate and rotate thereon. In addition, there may be a thin, low-friction coating applied to the foot pedal platform (or foot pedal assembly) to facilitate low friction sliding when desired. The foot pedal assembly may include one or more electromagnets that can be turned "on" or "off" to "engage" or "disengage" the assembly with the platform. For example, the electromagnets may be embedded in the pedal base of the foot pedal assembly, and activated by either a foot action (e.g., lifting the foot and pressing a button) or a hand action (e.g., using a wired or wireless connection) of the user. When the electromagnets are activated (e.g., turned "on"), the foot pedal assembly is engaged or locked to the foot pedal assembly platform at the position in which the electromagnets are activated. To move (e.g., reposition) the foot pedal assembly from this engaged or locked position to another position, the electromagnets are de-activated (e.g., turned "off"). This, in turn, disengages or unlocks the foot pedal assembly from the foot pedal assembly platform, and allows the user to move the foot pedal assembly to another position. It should be understood that the foot pedal assembly may be moved (e.g., translated or rotated) to any number of positions and/or orientations depending on the desire of the user, and locked at any of the positions. In other words, the positions are not discrete, predetermined or otherwise a number of preset positions, but rather dynamically determined based on the desire and/or ergonomic needs of the user, and the assembly is lockable at each position.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
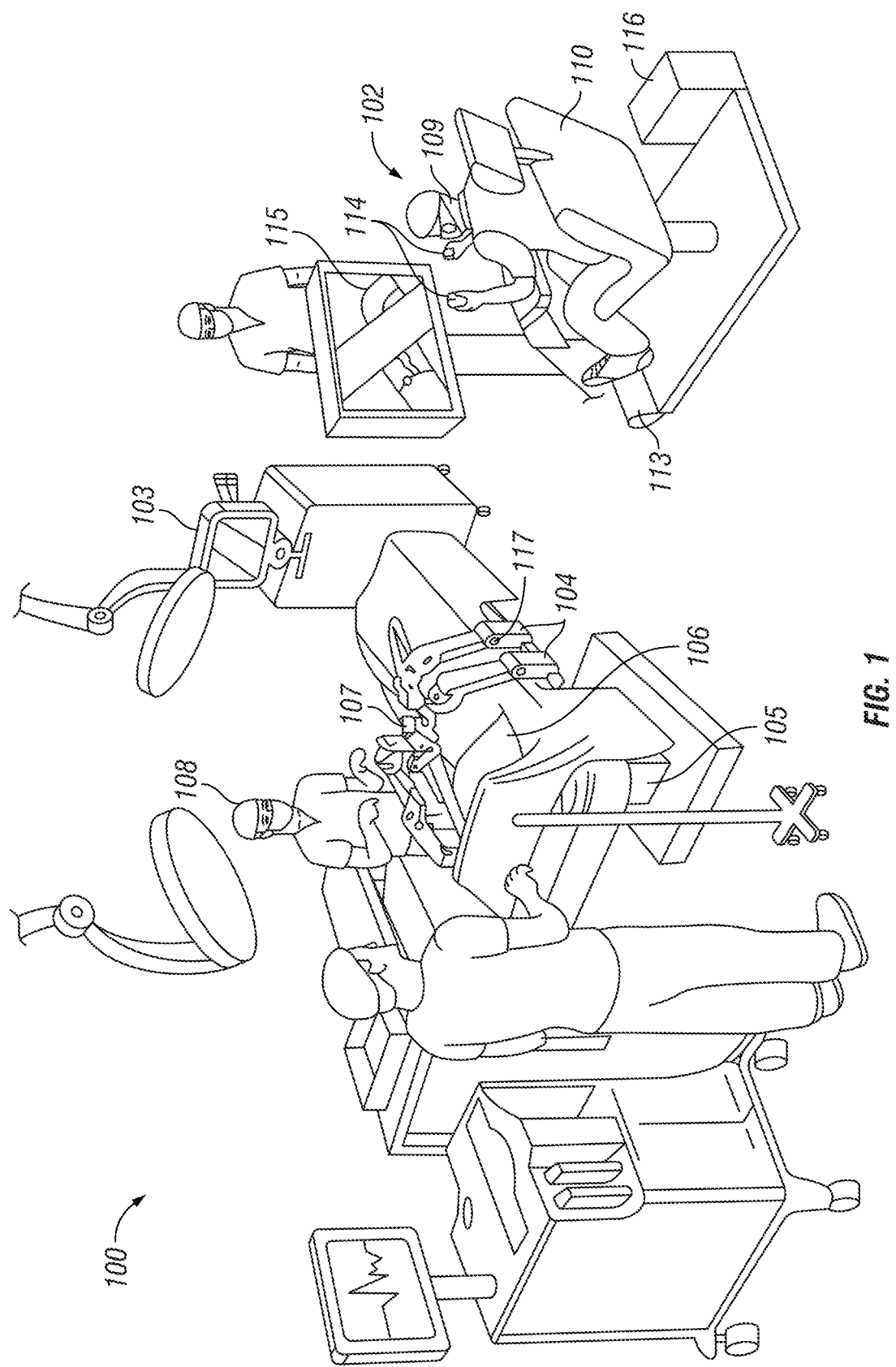
FIG. 1 is a pictorial view of one embodiment of a surgical robotic system in an operating arena.

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive. In addition, the term "and" as used herein in reference to different operations being performed by the same system or assembly, should be interpreted to mean the operations can both be performed by the system or assembly, but does not require the operations be performed at the same time. For example, a system or assembly that performs operations "A and B" can perform them at different times (e.g., sequentially), or at the same time.

In addition, the phrase "configured to," as used herein, may be interchangeable with, or otherwise understood as referring to, for example, a device that is "suitable for", "having the capacity to", "designed to", "adapted to", "made to", or otherwise "capable of" operating together with another device or other components. For example, a "processor configured to perform A, B, and C" may refer to a processor (e.g., a central processing unit (CPU) or an application processor) that may perform operations A, B and C by executing one or more software programs which stores a dedicated processor (e.g., an embedded processor) for performing a corresponding operation.

Referring to FIG. 1, FIG. 1 illustrates a pictorial view of an example surgical robotic system 100 in an operating arena. The surgical robotic system 100 includes a user console 102, a control tower 103, and one or more surgical robotic arms 104 at a surgical platform 105, e.g., a table, a bed, etc. The surgical robotic system 100 can incorporate any number of devices, tools, or accessories used to perform surgery on a patient 106. For example, the surgical robotic system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The surgical robotic arms 104 are shown as a table-mounted system, but in other configurations the surgical arms 104 may be mounted in a cart, ceiling or sidewall, or in another suitable structural support.

Generally, a remote operator 109, such as a surgeon or other operator, may use the user console 102 to remotely manipulate the surgical arms 104 and/or the attached surgical tools 107, e.g., teleoperation. The user console 102 may be located in the same operating room as the rest of the surgical robotic system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user interface devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the surgical arms 104 and the surgical tools 107 (that are mounted on the distal ends of the surgical arms.)

In some variations, the bedside operator 108 may also operate the surgical robotic system 100 in an "over the bed" mode, in which the beside operator 108 (user) is now at a side of the patient 106 and is simultaneously manipulating a robotically-driven tool (end effector as attached to the surgical arm 104), e.g., with a handheld UID 114 held in one hand, and a manual laparoscopic tool. For example, the bedside operator's left hand may be manipulating the handheld UID 114 to control a surgical robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the surgical robotic system 100 are in a stowed configuration or withdrawn configuration (to facilitate access to the surgical site.) Once access is completed, initial positioning or preparation of the surgical robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the surgical arms 104. Non-sterile personnel may also be present to assist the remote operator 109 at the user console 102. When the procedure or surgery is completed, the surgical robotic system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the surgical robotic system 100. The UID 114 may be communicatively coupled to the rest of the surgical robotic system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The surgical robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

Surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the surgical robotic system 100. The surgical robotic system 100 may include a right surgical arm 104 that is secured to the bed or table to the right side of the patient, and a left surgical arm 104 that is at the left side of the patient. An actuator 117 may include one or more motors that are controlled so that they drive the rotation of a joint of the surgical arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the surgical platform 105 and the user console 102 may be through a control tower 103, which may translate user commands that are received from the user console 102 (and more particularly from the console computer system 116) into robotic control commands that are transmitted to the arms 104 on the surgical platform 105. The control tower 103 may also transmit status and feedback from the surgical platform 105 back to the user console 102. The communication connections between the surgical platform 105, the user console 102, and the control tower 103 may be via wired and/or wireless links, using any suitable ones of a variety of data communication protocols. Any wired connections may be optionally built into the floor and/or walls or ceiling of the operating room. The surgical robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
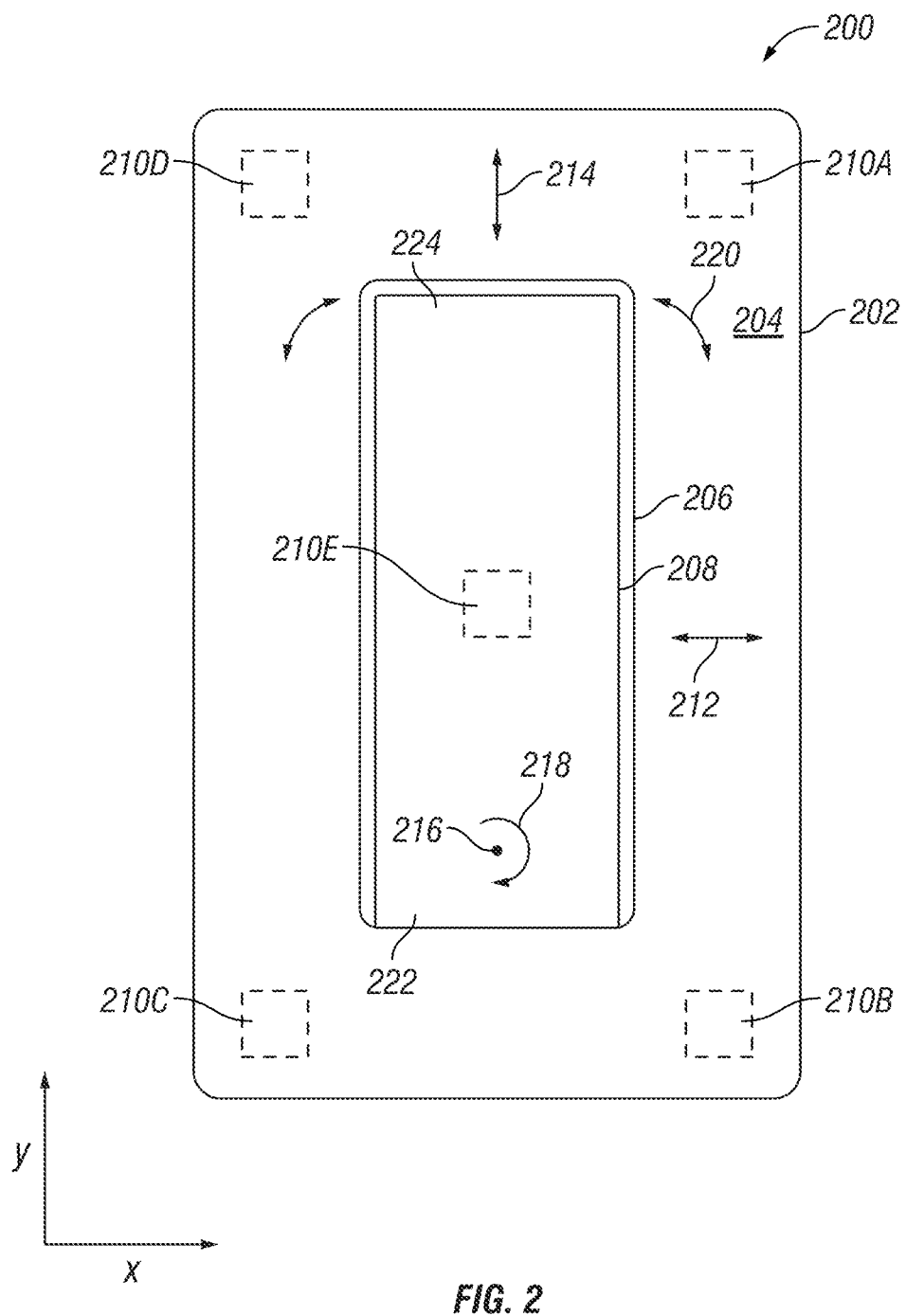
FIG. 2 is a top plan view of an embodiment of a foot pedal assembly.

A foot-operated control including a foot pedal assembly or system that can slide between activation positions and/or be repositioned to a desired location and/or orientation will now be described. Referring now to FIG. 2, FIG. 2 illustrates a top plan view of one embodiment of a foot pedal assembly 200 that can be used to control, or otherwise actuate, a surgical robotic operation of the surgical robotic system 100 (e.g., an operation of the surgical robotic arm 104). Foot pedal assembly 200 may include a foot pedal platform 202, a foot pedal base 206 and a foot pedal 208. The foot pedal platform 202 may include a contact surface 204, which the foot pedal base 206 contacts and is movably coupled to. The foot pedal 208 may be movably coupled to the foot pedal base 206. The term "foot pedal" is generally intended to refer to any type of foot-operated lever that can be used to control the robotic operation. The foot pedal base 206 may be any type of structure suitable for supporting the pedal. The foot pedal platform 202 may be any type of structuring having a surface (e.g., planar contact surface 204) across which the base 206 can move or slide. In addition, it should be understood that while a "foot pedal" and "foot pedal base" and "foot pedal platform" are described and shown herein in the context of a foot, the pedal, base and platform should be understood to cover any sort of lever and support member assembly that can be used in a similar manner by any body part, machine, robotic assembly, or the like to actuate or otherwise control a surgical robotic operation (or other operations requiring a pedal and base assembly). In some cases, the foot pedal 208 may be considered pivotally or rotatably coupled to the foot pedal base 206. In other cases, the foot pedal 208 may be, for example, a floating pedal that remains relatively parallel to the base 206, and moves up and down. FIG. 2 is intended to illustrate an embodiment where the foot pedal 208 is pivotally or rotatably coupled to the foot pedal base 206. Representatively, foot pedal 208 and/or foot pedal base 206 include an axle, pivot point, or axis of rotation, around which foot pedal 208 rotates or pivots as will be described in more detail in reference to FIG. 7.

In addition, foot pedal base 206 may move relative to foot pedal platform 202 between an arrangement of activation positions 210A, 210B, 210C, 210D and 210E on foot pedal platform 202. The activation positions 210A-210E correspond to different surgical robotic functions, operations or tasks (e.g., energy or non-energy functions, operations or tasks) that can be controlled by foot pedal assembly 200 when it is activated (e.g., pressed). Representatively, foot pedal base 206 may translate along at least two axes, for example, an x-axis and a y-axis to and/or between the activation positions 210A-210E. For example, foot pedal base 206 may slide across the contact surface 204 of foot pedal platform 202 in the directions illustrated by arrows 212 and 214 from one activation position (e.g., activation position 210E) to another activation position (e.g., activation positions 210A-210D). In addition, in some cases, foot pedal base 206 may pivot or rotate relative to foot pedal platform 202 around pivot point 216 (or a z-axis), as illustrated by arrow 218. In this aspect, the foot pedal base 206 (and foot pedal 208) is considered operable to both translate and rotate (e.g., sequentially or simultaneously) relative to foot pedal platform 202, between activation positions 210A-210E. In addition, since the single pedal assembly can move (e.g., slide) between activation positions 210A-210E and be activated at the different positions, the user can control four or more distinct robotic operations without having to move there foot between different pedals.

Figure 3:
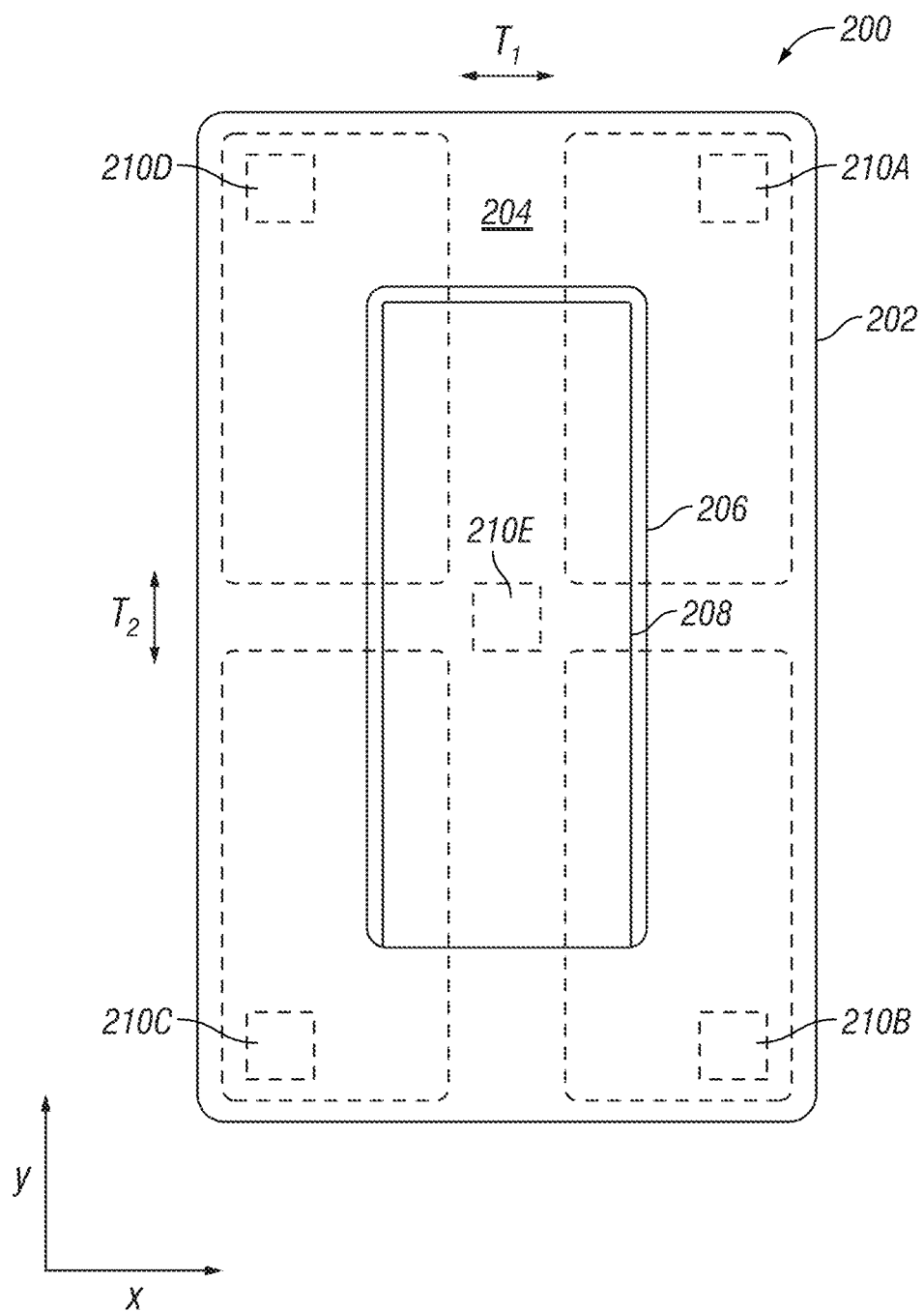
FIG. 3 is a top plan view of an embodiment of a foot pedal assembly.
Figure 4:
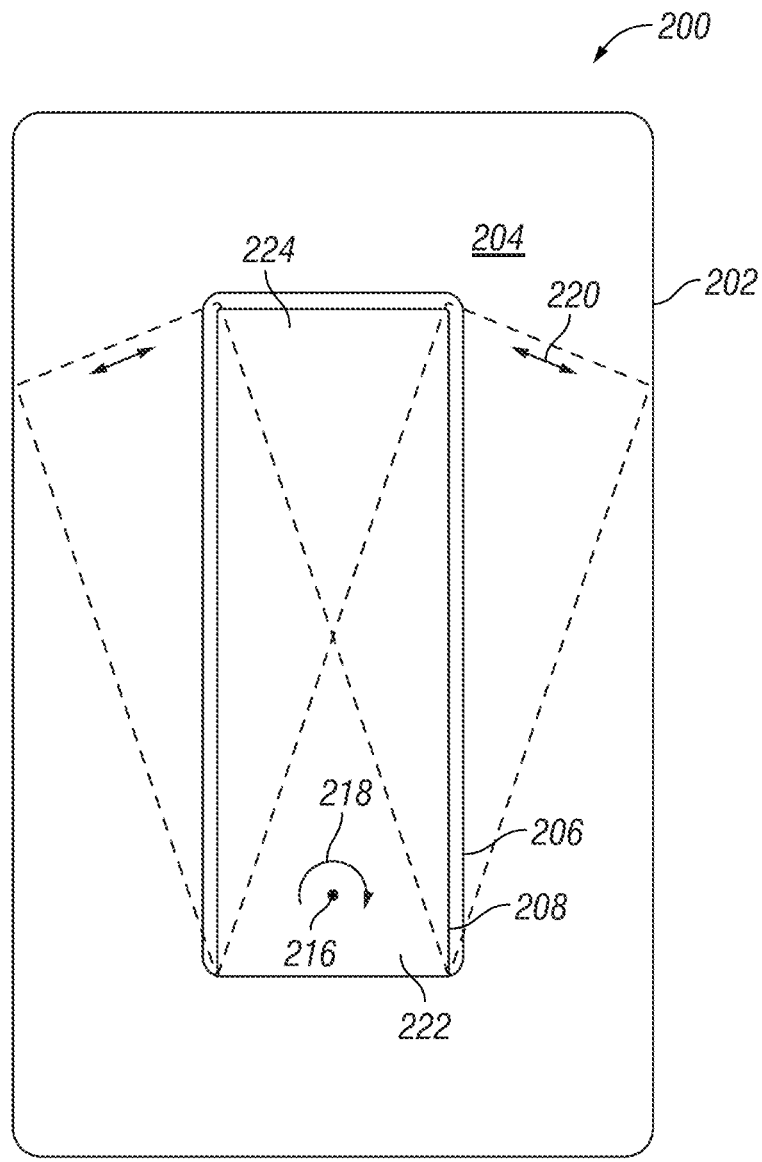
FIG. 4 is a top plan view of an embodiment of a foot pedal assembly.

Representatively, FIG. 3 and FIG. 4 are top plan views of the foot pedal assembly 200 translated and rotated, respectively, relative to foot pedal assembly platform 202, to the different activation positions 210A-210E. Representatively, FIG. 3 illustrates an embodiment in which activation positions 210A-210D are located near the four corners of foot pedal base 206, and the fifth activation position 210E is near the center of foot pedal base 206. As previously discussed, each of activation positions 210A-210E may be correlatable to different surgical robotic operations. For example, the activation positions 210A and 210B along the right side of foot pedal platform 202 may be correlatable to surgical robotic operations, functions or tasks which, in a typical pedal assembly, are controlled by two different pedals along a right side of a pedal bank (e.g., activate energy or advanced tools such as lasers, staplers, etc.). Similarly, activation positions 210C and 210D along the left side of foot pedal platform 202 may be correlatable to surgical robotic operations typically controlled by two different pedals along a left side of a pedal bank (e.g., cameras). The activation position 210E may be correlatable to a fifth surgical robotic operation (e.g., a clutch function). During operation, foot pedal 208 and foot pedal base 206 may be, in one embodiment, initially at a center position over activation position 210E, and then translated as illustrated by arrows $T_1$ and/or $T_2$ to activation positions 210A-210D. The different foot pedal 208 and foot pedal base 206 positions are illustrated by dashed lines. The activation positions 210A-210E may be, or otherwise include, sensors that detect the presence of the foot pedal base 208 at the position. When the foot pedal 208 is then activated at the position (e.g., rotated or pivoted with respect to base 206) a signal mapping the position to the desired operation or function is sent to a processor or controller to control the desired surgical robotic operation. The sensors may be any type of position sensor capable of being connected to, or otherwise positioned on, the foot pedal platform 202 and detecting a presence of a foot pedal base 206. For example, the sensor may be a proximity sensor, a pressure sensor, a capacitive sensor, or the like.

In addition, it should be understood that while the activation positions 210A-210E are shown confined to the corners of foot pedal platform 202, they may extend across a much larger region of the foot pedal platform 202 such that foot pedal base 206 does not have to be moved all the way to a corner of foot pedal assembly platform 202 to control the corresponding surgical robotic operation. For example, the contact surface 204 of foot pedal platform 202 may be divided into four or five equal parts, and each of the activation positions 210A-210D may extend across an entire part such that foot pedal platform 206 need only overlap a portion of the position to be at the activation position and control the desired robotic operation. In any case, regardless of the size of the activation position, it should be understood that the arrangement of activation positions 210A-210E allows for the user to activate four or more distinct robotic functions using a single pedal assembly.

As previously discussed, the foot pedal 208 in combination with foot pedal base 206 may also rotate or pivot relative to foot pedal platform 202. The various rotated or pivoted positions are illustrated by FIG. 4. Representatively, foot pedal 208 and foot pedal base 206 can pivot or rotate about point 216 (e.g., a z-axis) as illustrated by arrow 218, to a position to the right of center or the left of center as illustrated by arrow 220. In some cases, pedal 208 and foot pedal base 206 may rotate or pivot from the center position (e.g., activation position 210E) to the different activation positions 210A-210D, without translation, to control a desired operation or function. In other cases, foot pedal 208 and foot pedal base 206 may both translate and rotate (or pivot), for example, translate to one activation position as shown in FIG. 3 (e.g., activation position 210A), and then rotate from that position to another adjacent activation position (e.g., activation position 210D) to control another operation or function. In still further cases, the rotation may be a more passive rotation used to achieve a more comfortable pedal orientation for the user (e.g., to angle the pedal) while at the desired activation position, without activating another position.

Figure 5:
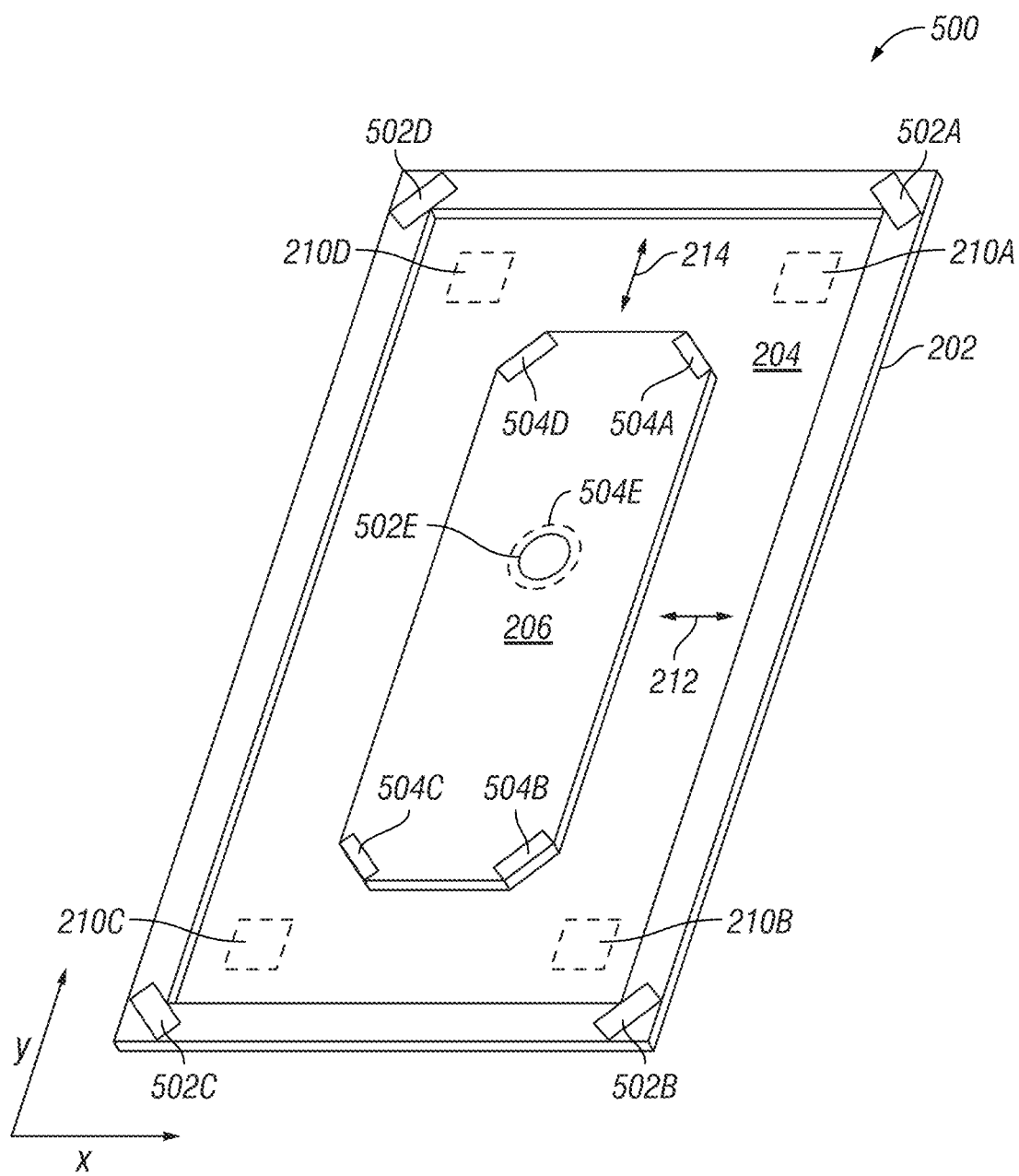
FIG. 5 is a side perspective view of an embodiment of a foot pedal assembly.
Figure 6:
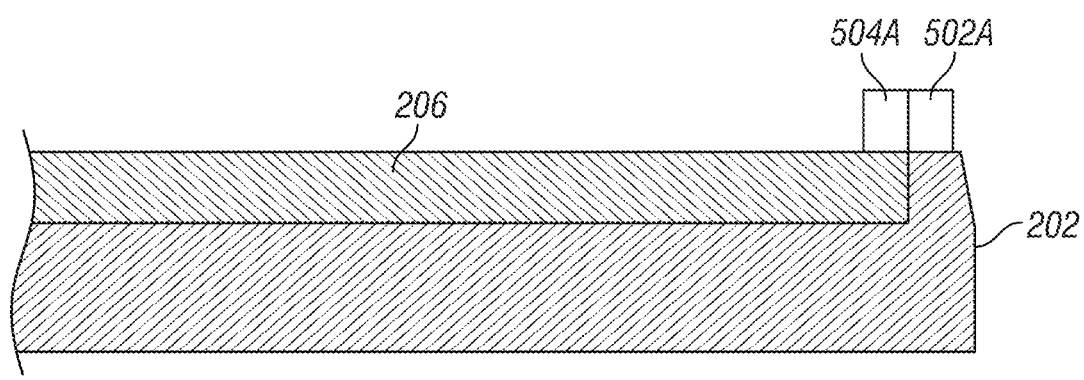
FIG. 6 is a cross-sectional side view of an embodiment of a foot pedal assembly.

The foot pedal assembly 200 may further include a "snap to" or locking assembly which locks, or otherwise snaps, holds or secures, the foot pedal base 206 at the desired activation position 210A-210E. FIG. 5 illustrates one embodiment of a locking assembly 500 of the foot pedal assembly 200. Representatively, locking assembly 500 may include an arrangement or assembly of platform magnets 502A, 502B, 502C, 502D and 502E connected, or otherwise attached to, foot pedal platform 202 near the activation positions 210A-210E. For example, platform magnets 502A-502E may be attached to pedal platform 202 near each of the corners and at the center. For example, attached to a protrusion, or other surface, of platform 202, such as by an adhesive or mechanical attachment mechanism as discussed in more detail with respect FIG. 8. In addition, locking assembly 500 may include an arrangement or assembly of complimentary pedal base magnets 504A, 504B, 504C, 504D and 504E near corners and a center of base 206, which interface with the corners and center of pedal platform 202. For example base magnets 504A-504E may be attached a protrusion, or other surface, of pedal platform 202, such as by an adhesive or mechanical attachment mechanism as discussed in more detail with respect FIG. 8. Platform magnets 502A-502E and base magnets 504A-504E may, for example, be permanent magnets that are arranged to have opposite poles interfacing one another. In this aspect, when pedal base 206 is moved to one of activation positions 210A-210E, one of the corresponding platform magnets 502A-502E is positioned near a complimentary one of base magnets 504A-504E. The magnets 502A-502E and 504A-504E, in turn, attract one another and "snap" (or otherwise secure) pedal base 206 to foot pedal platform 202 at the desired position, using a magnetic force. The attachment of pedal base 206 to pedal platform 202 using locking assembly 500 is illustrated by FIG. 6. Representatively, one of platform magnets 502A-502E, namely platform magnet 502A and one of platform magnets 504A-504E, namely base magnet 504A, are shown attached to one another in FIG. 6.

Figure 7:
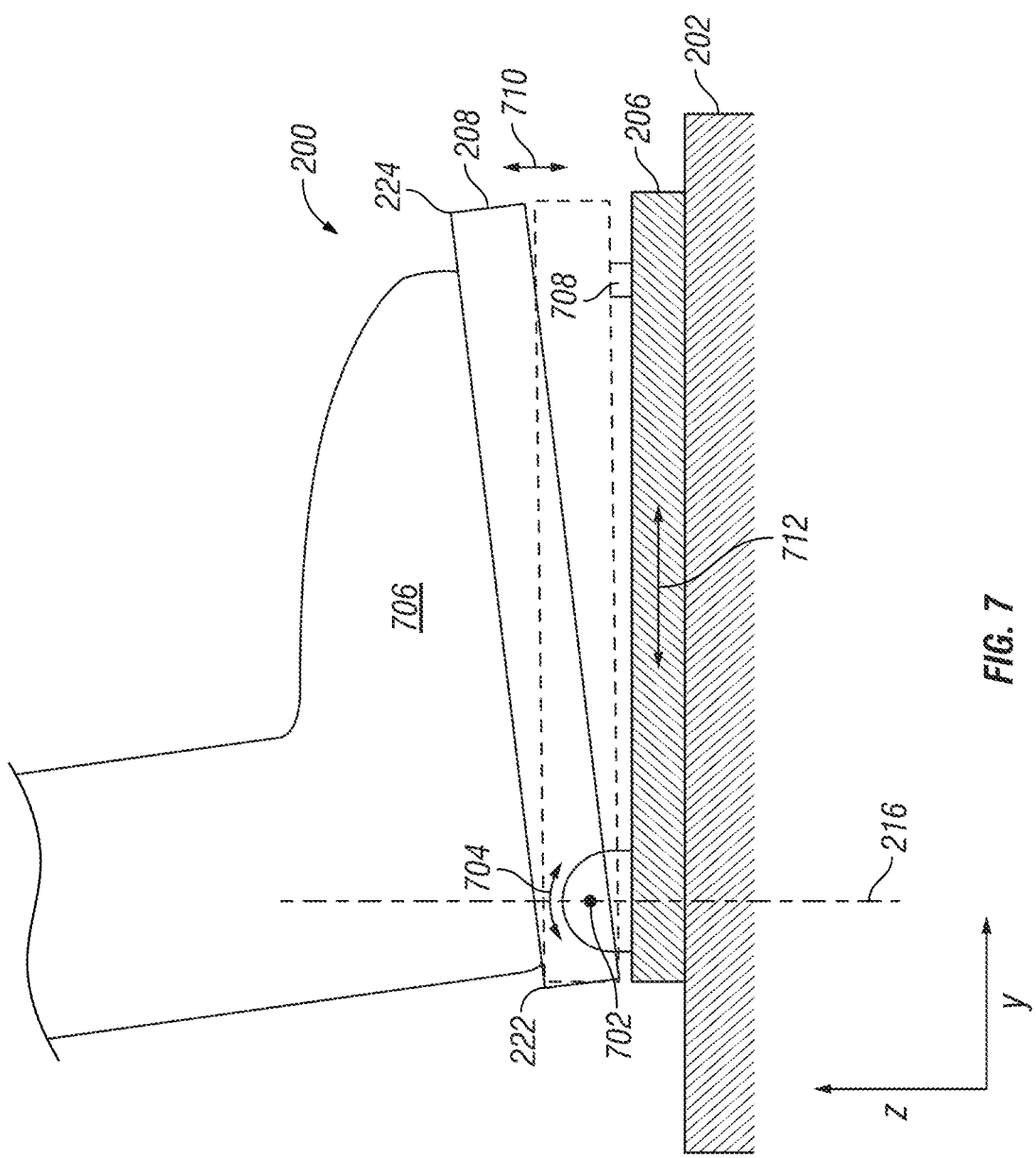
FIG. 7 is a side view of an embodiment of a foot pedal assembly.

FIG. 7 is a side view of further aspects of foot pedal assembly 200. From this view, the rotation or pivoting motion of foot pedal 208 relative to foot pedal base 202 can be more clearly seen. Representatively, FIG. 7 shows the pivoting (or rotation) of foot pedal 208 around axle 702, as shown by arrow 704. For example, foot pedal 208 moves from a "neutral" position in which it is at an angle with respect to foot pedal base 206, to an "active" position in which the distal end 224 of foot pedal 208 is closer to foot pedal base 206 (as illustrated by dashed lines). Representatively, foot pedal 208 may be considered to be in a "neutral" position when it is not causing, actuating, or otherwise controlling, a robotic operation (e.g. an operation of the surgical robotic arm 104). On the other hand, foot pedal 208 may be considered to be in an "active" position when it is closer to foot pedal base 206, because in this position, foot pedal 202 is causing, actuating, or otherwise controlling, a robotic operation (e.g., an operation of the surgical robotic arm 104). For example, in the more horizontal position (as illustrated by the dashed line) foot pedal 208 may contact switch 708, which, in turn, sends a signal to a control system (e.g., a console processor of the console computer system 116) to actuate, or otherwise control, the robotic operation. In this aspect, foot pedal 208 may be referred to herein as being "active", "activated" or "actuated" when in the more horizontal position (e.g., a position achieved when a user's foot presses on the pedal), and "neutral" or "inactive" when in the angled position (e.g., the resting position prior to the user's foot contacting the pedal). In addition, it should be understood that while a single switch 708 and/or activation features is described, it is contemplated that foot pedal assembly 200 may have multiple switches, mechanical detents, nonlinear force profiles, or other similar features, which provide for multi-stage activation capabilities.

Referring now in more detail to foot pedal 208, foot pedal 208 may include a proximal portion or end 222 and a distal portion or end 224. During operation, the proximal portion 222 will be near the heel of the foot 706, and the distal portion 224 will be farther from the heel (e.g., closer to the toe). The foot pedal 208 may include a substantially flat or planar surface that, in the neutral pedal position, may be angled, and face away from, pedal base 206. On the other hand, in the active pedal position (e.g., when a user's foot contacts foot pedal 208), the surface may be rotated such that it is substantially parallel to, or the distal end 224 is otherwise closer to, base portion 206. For example, foot pedal 208 may be manually moved (e.g., rotate, pivot, move up/down) with respect to foot pedal base 206 when a force or pressure is applied the pedal surface as illustrated by arrow 710.

In some embodiments, an active feedback mechanism may further be included in the assembly 200 to provide an indication to the user of the pedal position. For example, the active feedback mechanism could be a motorized actuator or sensor which is part of, or otherwise incorporated into, switch 708. The feedback mechanism may output a haptic response to the user (e.g., vibration) when the foot pedal 208 contacts switch 708. Alternatively, or additionally, the active feedback mechanism could be incorporated anywhere within foot pedal assembly 200 and used to output a response to the user to indicate other operations relating to foot pedal assembly 200. For example, the feedback mechanism could be integrated into, or positioned near, the activation positions 210A-210E (e.g., part of the corresponding sensors) or magnet assemblies 502A-502E or 504A-504E to indicate to the user when the foot pedal base 206 (and foot pedal 208) is nearing, or otherwise aligned with, activation positions 210A-210E.

In addition, in this embodiment, axle 702 is positioned at the proximal end 222, or at least closer to the proximal end 222 than the distal end 224, of foot pedal 208 (and foot pedal base 206). In this aspect, the user rocks their foot forward and presses their toe against foot pedal 208, as opposed to the heel, to pivot or rotate foot pedal 208 to the activated position. In addition, since pressing on the heel does not pivot (or rotate) foot pedal 208 about axle 702, or otherwise activate the pedal assembly, the user's heel can be used to translate (e.g., slide) foot pedal base 206 relative to foot pedal platform 202, as illustrated by arrow 712 without the risk of unintentional activation. For example, the user can press the heel of their foot 706 against the proximal end 222 of foot pedal 208 (while their toes rest on the distal end 224) to apply a force in a direction of arrow 712 and translate the foot pedal base 206 along the y-axis as shown (or the x-axis).

In addition, the user's heel can be used to rotate (or pivot) pedal 208 (and pedal base 206) around pivot point 216 (or z-axis) without the risk of unintentional activation. For example, while the heel is resting on the proximal end 222 of foot pedal 208, the user can rotate (or pivot) their heel clockwise or counterclockwise. This, in turn, rotates (or pivots) foot pedal 208 around the pivot point or axis 216 (z-axis), and in turn the distal end 224 to the right or left of center. In some cases, this rotation of foot pedal 208 may be used to achieve a more desirable ergonomic position. In other cases, it may be used to reposition foot pedal 208 to an activation position and control a surgical robotic operation. In addition, it should be recognized that in other embodiments, instead of rotation of the entire foot pedal 208 and foot pedal base 206 relative to foot pedal platform 202 as illustrated, this heel rotation functionality may be achieved with a rotating foot panel.

Figure 8:
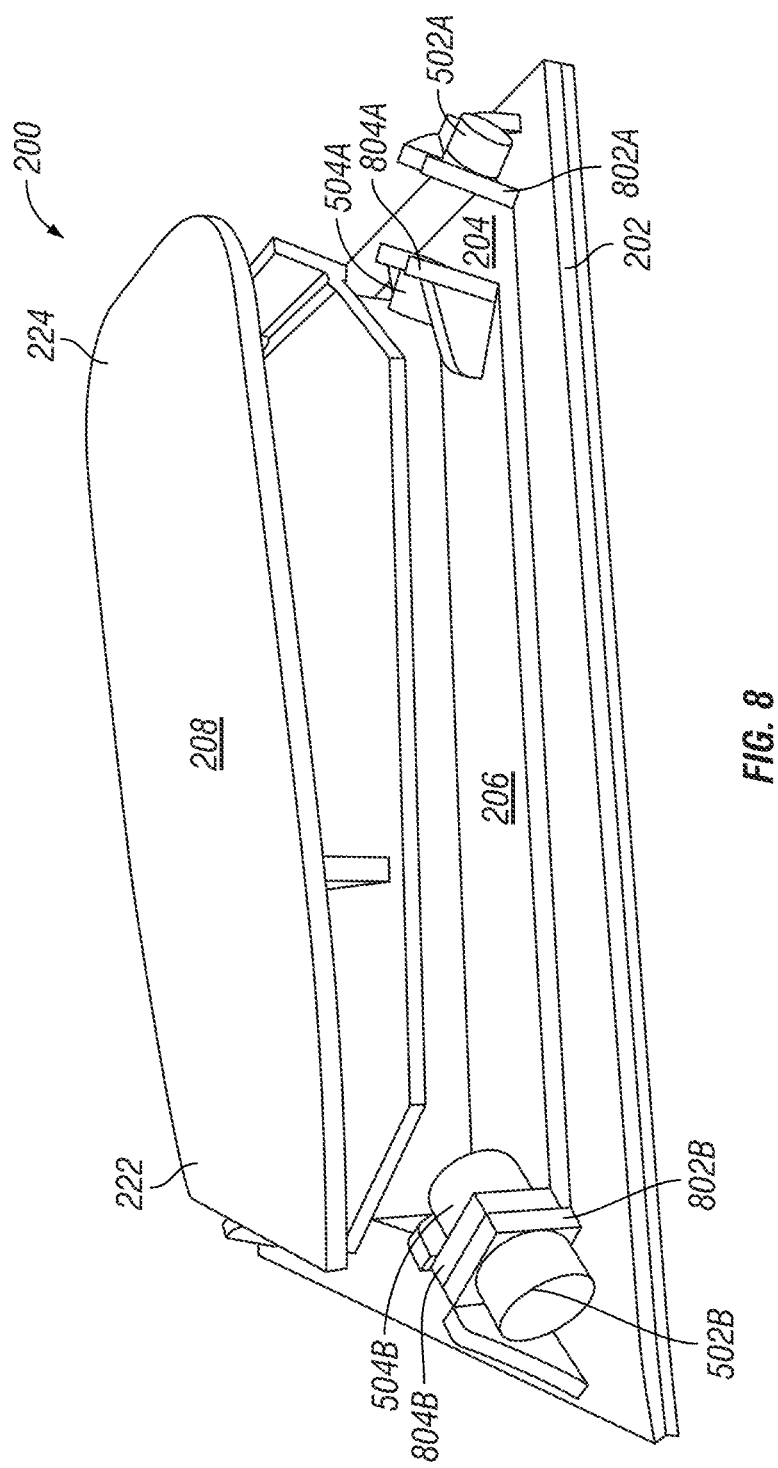
FIG. 8 is a side perspective view of an embodiment of a foot pedal assembly.
Figure 9:
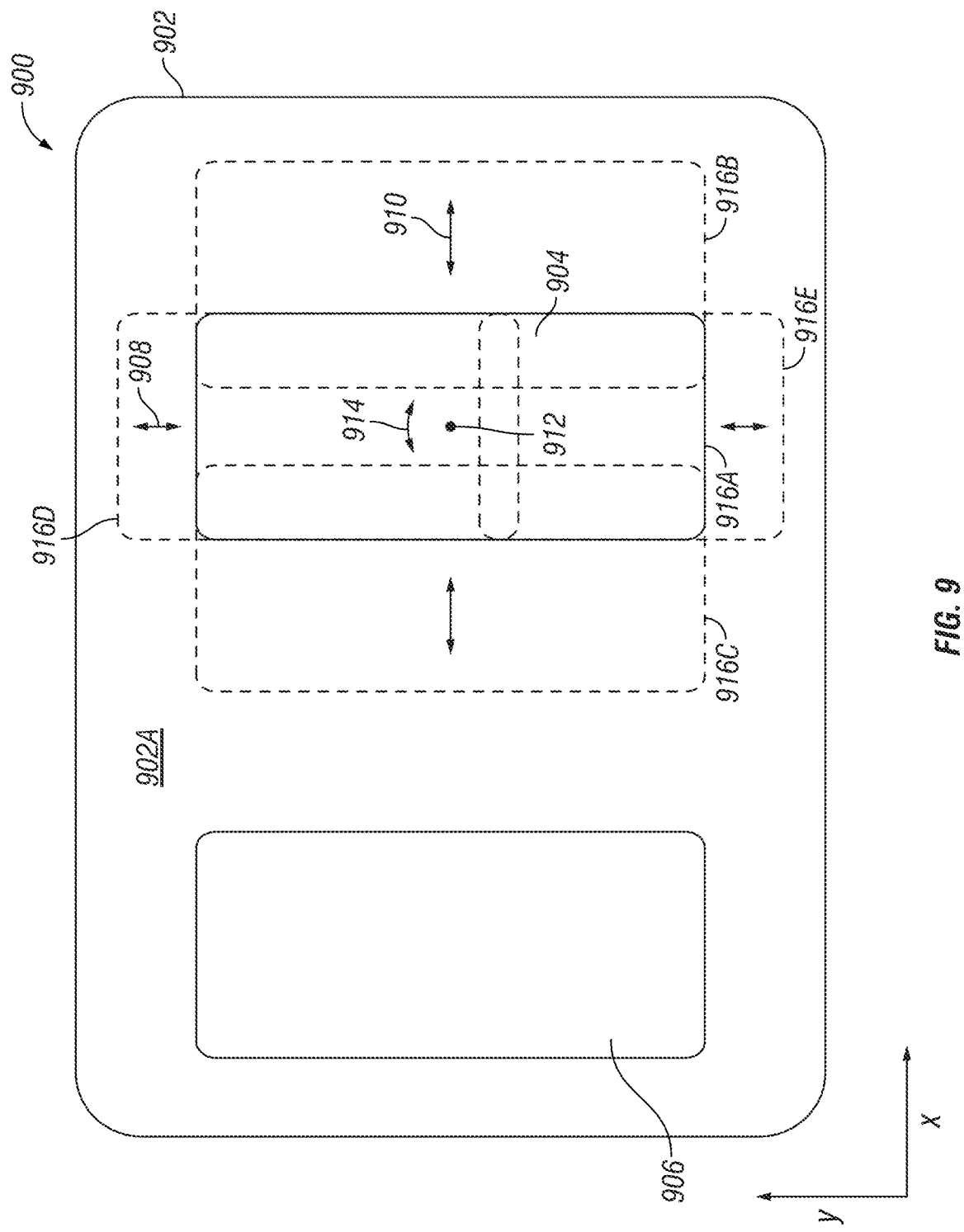
FIG. 9 is a top plan view of an embodiment of a foot pedal system.

FIG. 8 is a side perspective view of an embodiment of a foot pedal assembly. Representatively, FIG. 8 illustrates foot pedal assembly 200 having foot pedal platform 202, foot pedal base 206 and foot pedal 208. From this view, it can be seen that the platform magnets 502A, 502B are secured to protrusions 802A, 802B, respectively, extending from a surface of foot pedal platform 202. In addition, base magnets 504A, 504B are secured to protrusions 804A, 804B, respectively, extending from a surface of foot pedal base 206. The protrusions 802A, 802B and protrusions 804A, 804B align with one another when the foot pedal base 206 is positioned near one of the corresponding corners of foot pedal platform 202. This, in turn, aligns one of the platform magnets 502A-502B with one of the base magnets 504A-504B, to thereby "snap" (or hold) the pedal assembly at the desired activation position. In one embodiment, the platform magnets 502A-502B are attached to exterior surfaces of protrusions 802A-802B, and the base magnets 504A-504B are attached to interior surfaces of protrusions 804A-804B. In this aspect, in the locked or "snapped" position shown, protrusions 802A-802B, 804A-804B are between magnets 502A-502B, 504A-504B, respectively. In other cases, magnets 502A-502B, 504A-504B may be attached to any surface of the protrusions 802A-802B, 804A-804B, foot pedal platform 202, or foot pedal base 206 which allows for sufficient magnetic force between magnets to hold and/or release foot pedal base 206 at the activation position. Although not shown in this view, the remaining platform magnets 502C-502E and base magnets 504C-504E may be secured to similar protrusions at the remaining corners of foot pedal platform 202 and pedal base 206, respectively.

FIG. 9-FIG. 12 illustrate embodiments of a selectively locking, repositionable foot pedal system. Representatively, foot pedal system 900 is configured to allow the user to reposition a foot pedal assembly (e.g., pedal assembly 200), and in some cases one foot pedal assembly per foot, to a desired location and orientation, and then lock it in place as desired. In this aspect, the user can keep their feet on a respective foot pedal assembly (eliminating the need to locate pedals when activation is desired) while also enabling them to change that location throughout a procedure or task. This, in turn, addresses the ergonomic need of a user to reposition their feet occasionally during a procedure while seated.

Referring now in more detail to the foot pedal system 900, foot pedal system 900 includes a foot pedal assembly platform 902 and foot pedal assemblies 904, 906. In some embodiments, foot pedal assembly platform 902 may be a structure that is part of the user console (e.g. user console 102) and has a substantially planar surface 902A on one side for supporting the foot pedal assemblies 904, 906. In other embodiments, foot pedal assembly platform 902 and surface 902A may be formed by the surgical room floor itself, for example, where the pedal assemblies are detached from the user console. Foot pedal assemblies 904, 906 may be movably (e.g., slidably), positioned on surface 902A of the foot pedal assembly platform 902 and moved with respect to foot pedal assembly platform 902 to any platform or ergonomic position that meets the user's ergonomic needs. Representatively, foot pedal assembly 904 (and/or foot pedal assembly 906) may be translated (e.g., slide) across surface 902A, as illustrated by arrows 908 and 910. For example, foot pedal assembly 904 may move from a first platform position (e.g., center position 916A) to a second platform position (e.g., right position 916B), or from one position to any number of other positions (e.g., positions 916C-916E). Similarly, although not shown, foot pedal assembly 906 may also be translated in the direction of arrows 908 and 910, similar to foot pedal assembly 904. It should further be understood that arrows 908 and 910 represent directions parallel to a y-axis and an x-axis, respectively, which are parallel to surface 902A. Foot pedal assemblies 904, 906 may also therefore be considered to translate along a y-axis and an x-axis to the desired positions. It should be understood, however, that the movement of foot pedal assemblies 904, 906 is not limited to the x-axis and/or y-axis, or directions parallel to these axes, rather the movement could be in any direction (e.g., diagonal) parallel to surface 902A.

Figure 10:
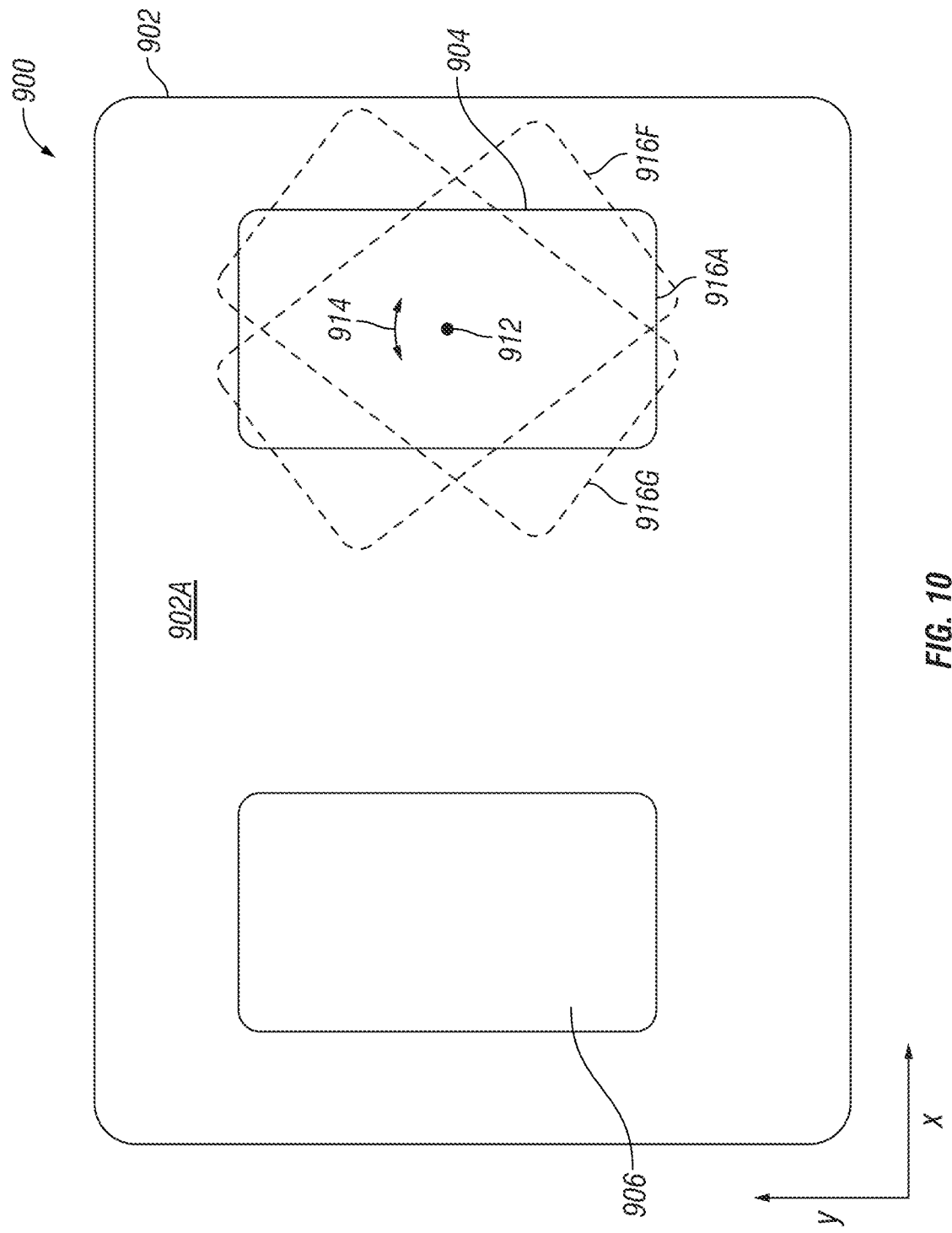
FIG. 10 is a top plan view of an embodiment of a foot pedal system.
Figure 11:
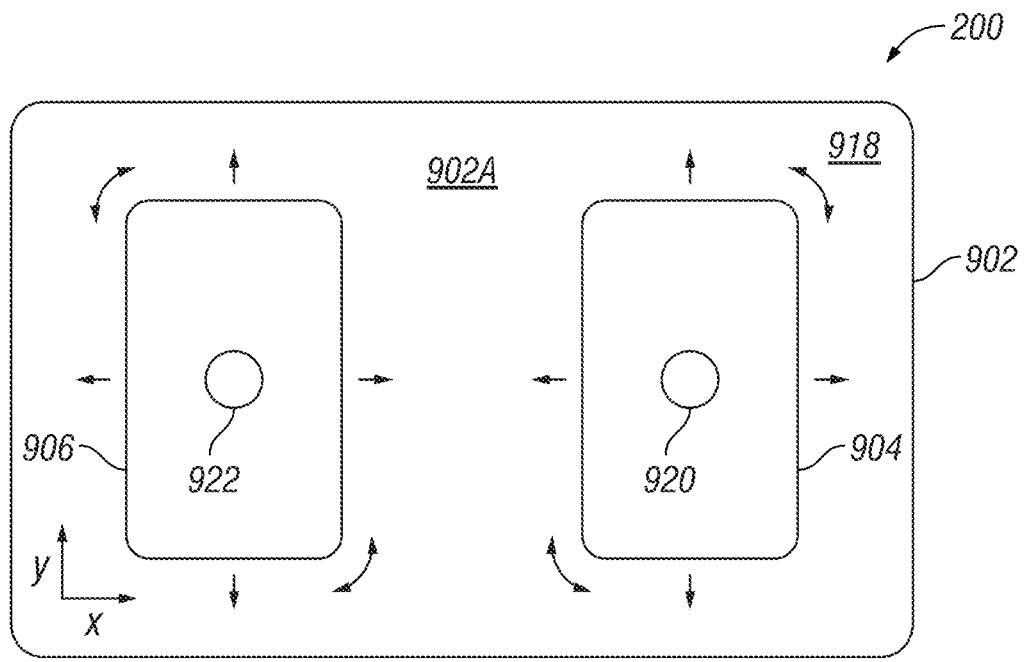
FIG. 11 is a top plan view of an embodiment of a foot pedal system.
Figure 12:
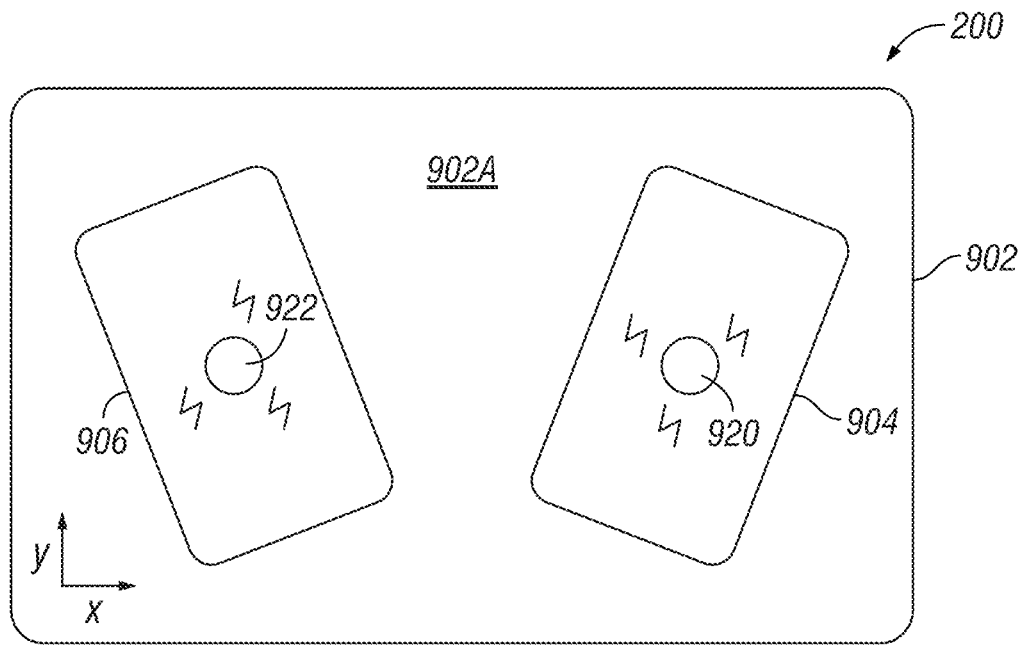
FIG. 12 is a top plan view of the foot pedal system of FIG. 11 with the foot pedal assembly repositioned.

In addition, foot pedal assembly 904 (and/or foot pedal assembly 906) may also be rotated around an axis or point 912. Representatively, 912 may represent an axis that is perpendicular (or normal) to the y-axis and x-axis as previously discussed. In other words, 912 may be a z-axis, and foot pedal assembly 904 (and/or foot pedal assembly 906) may rotate around the z-axis as illustrated by arrow 914 to different desired ergonomic positions 916F and 916G, as illustrated by FIG. 10. It should be understood that foot pedal assembly 904 (and/or foot pedal assembly 906) may be rotated while at the center position 916A as shown, however, may also be rotated at any of the different positions 916B-916E previously discussed in reference to FIG. 9. In this aspect, foot pedal assembly 904 and foot pedal assembly 906 may be repositioned to an unlimited number of ergonomic positions as desired by the user.

Once at the desired ergonomic position (e.g., any one of ergonomic positions 916A-916G), foot pedal assembly 904 (and/or foot pedal assembly 906) may be locked, or otherwise secured, in place. Representatively, foot pedal assembly system 900 may further include a locking assembly that holds foot pedal assembly 904 (and/or foot pedal assembly 906) in the desired position. Representatively, the locking assembly may include a first locking member 918 and a second locking member 920 or 922. In one embodiment, the locking assembly is an electromagnetic locking assembly. In this case, the first locking member 918 is a ferromagnetic plate and the second locking member 920 or 922 is an electromagnet attached to the foot pedal assembly 904 or foot pedal assembly 906, respectively. The ferromagnetic plate may be coupled to, or form, the surface 902A of the foot pedal assembly platform 902. In one embodiment, the electromagnet of the second locking member 920 (or member 922) may be embedded within foot pedal assembly 904 (or assembly 906). During operation, the electromagnets of the second locking members 920 (and 922) may be transitioned between an "off" or "disengaged" mode in which no magnetic field is generated, and an "on" or "engaged" mode in which a magnetic field is generated. In the "off" or "disengaged" mode shown in FIG. 11, there is no magnetic field holding the foot pedal assembly 904 (and/or foot pedal assembly 906) to platform 902, and therefore the user can reposition or move (translate or rotate) the foot pedal assembly 904 (and/or foot pedal assembly 906) to any desired position as illustrated by arrows. Once in the desired position, the locking assembly can be transitioned to the "on" or "engaged" mode, which essentially turns "on" the electromagnets (e.g., members 920, 922) causing them to generate a magnetic field and lock, or otherwise engage, the associated foot pedal assembly 904 (or 906) to the ferromagnetic plate of surface 902A using a magnetic force. The electromagnets of members 920, 922 may be activated by the user by a foot action (e.g., lifting the foot and pressing a button) or by a hand action (e.g., using a handheld controller having a wired or wireless connection to the foot pedal assembly). For example, there may be a selection on a surgeon bridge touch pad or in a graphical user interface, and the user uses the user input devices (UIDs) and pedals to navigate to and select the desired mode (to engage or disengage the electromagnet.

In other embodiments, the locking assembly may be an assembly that uses an electrostatic, suction, mechanical or any other force sufficient to engage and disengage the foot pedal assembly 904 with the foot pedal assembly platform 902. These alternative locking mechanisms could be particularly useful in embodiments where foot pedal assembly 904 (and/or foot pedal assembly 906) is detached from the user console and operated wirelessly from any location within the surgical room. For example, in one embodiment, the foot pedal assembly 904 (and/or foot pedal assembly 906) may be detached from the user console and wirelessly controlled from any location on the surgical room floor (e.g., near the operating table). Representatively, this configuration may be desirable in an over-the-bed laparoscopic operation. In this aspect, the surgical room floor may be the platform 902 that the pedal assembly 904 (and/or foot pedal assembly 906) engages or disengages with. The pedal assembly 904 (and/or foot pedal assembly 906) may have a suction mechanism integrated therein which. When activated, the suction mechanism may create a low pressure region between pedal assembly 904 and the floor (e.g., surface 902A) that secures the foot pedal assembly 904 (and/or foot pedal assembly 906) to the floor, and when de-activated, the pressure equalizes allowing foot pedal assembly 904 (and/or foot pedal assembly 906) to be repositioned.

In some cases, one or both of foot pedal assemblies 904, 906 may be foot pedal assembly 200 previously discussed in reference to FIG. 2-FIG. 10. As previously discussed, foot pedal assembly 200 is operable to be moved (e.g., rotated and translated) between activation positions (e.g., activation positions 210A-210E), and further pivoted to an active position to control a robotic operation. In addition, foot pedal assembly 200 is operable to be repositioned (e.g., rotated and translated) along foot pedal assembly platform 902 to achieve a desired ergonomic or platform position, as previously discussed in reference to assembly 904. Foot pedal assembly 200 (i.e., assemblies 902 and 904) therefore provides a single foot pedal assembly having several degrees of freedom that allow for repositioning between different activation positions and ergonomic positions, and control of different robotic functions, without the user having to lift their foot, or move their foot between different pedals.

Figure 13:
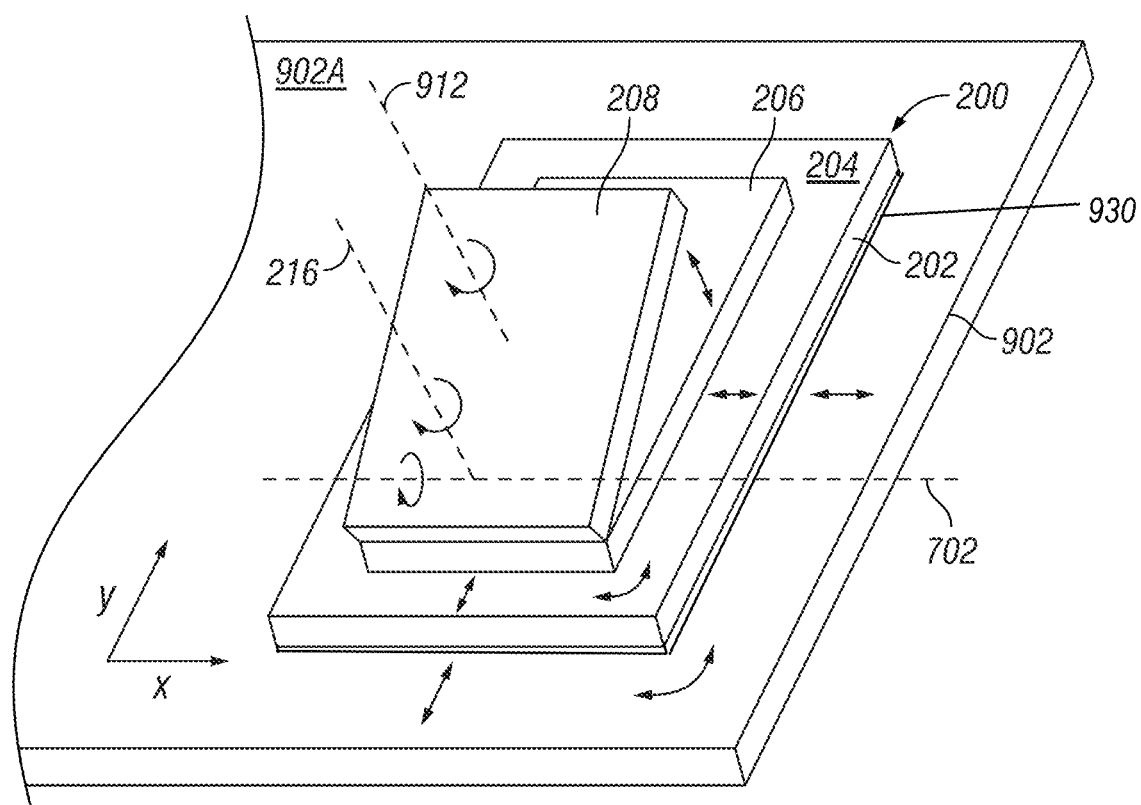
FIG. 13 is a perspective view of an embodiment of a foot pedal system.

Representatively, as illustrated in FIG. 13, foot pedal assembly 904 (or assembly 906) may be foot pedal assembly 200, including foot pedal platform 202, foot pedal base 206 and foot pedal 208. As previously discussed, foot pedal base 206 can translate (e.g., along the x-axis and the y-axis) and rotate or pivot (e.g., along the z-axis 216), relative to foot pedal platform 202, to a desired activation position (e.g., positions 210A-210E). In addition, foot pedal 208 can rotate or pivot (e.g., along the pivot point or axis 702) relative to foot pedal base 206 between neutral and active positions (once at the desired activation position) to control a robotic operation or function. Still further, foot pedal platform 202 can translate along surface 902A of foot pedal assembly platform 902 (e.g., along an x-axis and a y-axis) and pivot or rotate around axis 912 (e.g., z-axis), relative to foot pedal assembly platform 902 (as shown by the arrows), to any ergonomic or platform position desired by the user. In addition, foot pedal assembly 200 may be locked, or otherwise secured, at the desired activation position using a first locking assembly (e.g., magnet assembly) and locked, or otherwise secured, to the foot pedal assembly platform 902 at the desired platform or ergonomic position using a second locking assembly (e.g. electromagnet assembly). In addition, in some embodiments, the foot pedal assembly 200 (and/or foot pedal assemblies 904, 906) may also include a thin, low-friction coating 930 applied to an interface with the foot pedal assembly platform 902 to facilitate repositioning. For example, coating 930 may be a polytetrafluoroethylene (PTFE) coating, also known as Teflon®, graphite, or any other suitable low friction coating that can be applied to the desired interfacing. Representatively, in one embodiment, coating 930 may be applied to the surface of foot pedal platform 202 that interfaces with surface 902A of the foot pedal assembly platform 902. In other embodiments, the thin, low-friction coating 930 may be formed on surface 902A, or interfacing surfaces of both platform 202 and platform 902.

It should further be understood that while foot pedal assemblies 904, 906 are described as corresponding to assembly 200, assemblies 904, 906 may be any type of foot pedal assembly (e.g., a floating foot pedal assembly, a multifunctional pedal assembly, or the like) and repositionable relative to a platform, as described herein.

Figure 14:
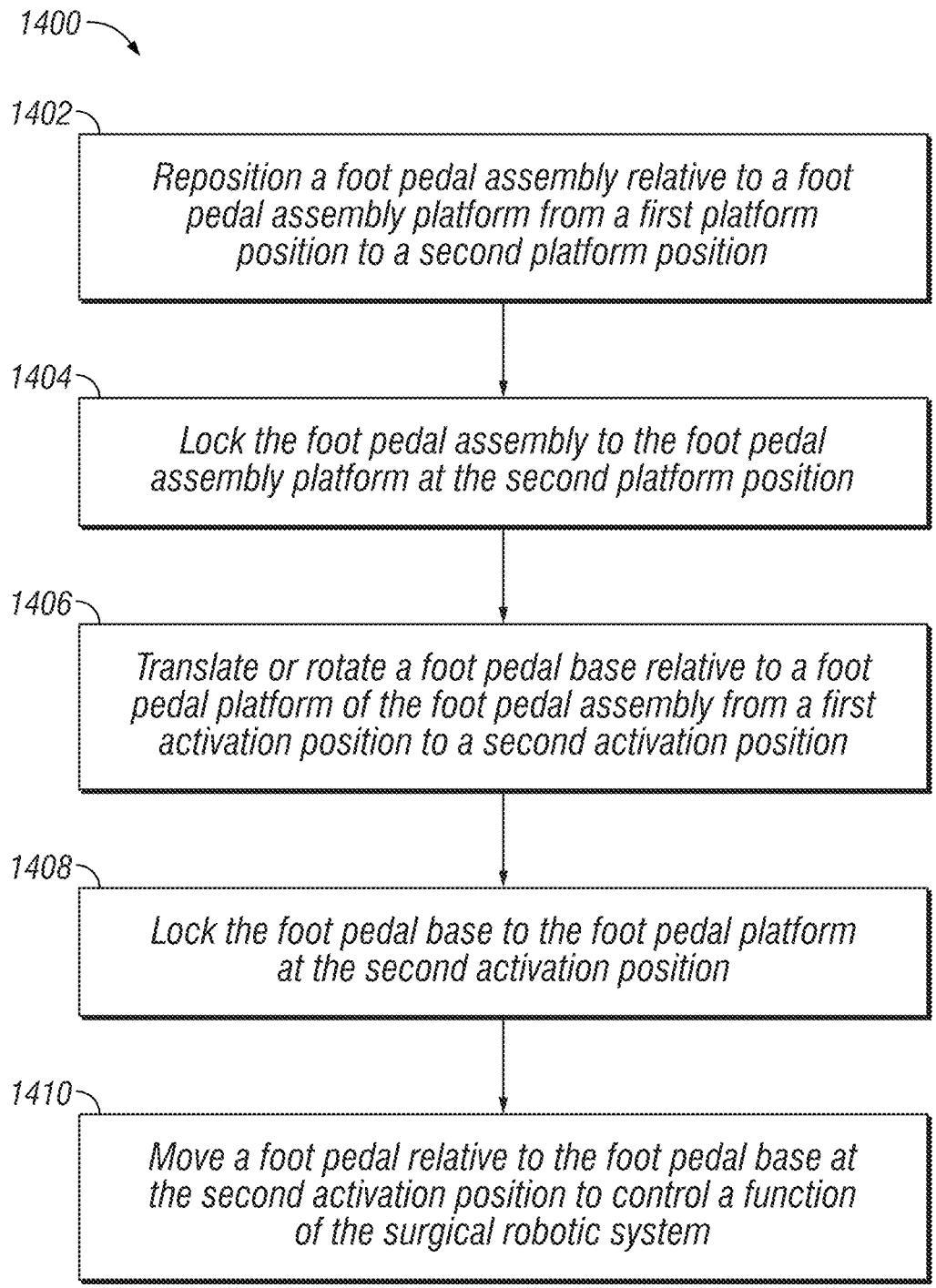
FIG. 14 is a flow chart of one embodiment of a process for repositioning and activating a foot pedal system.

FIG. 14 illustrates one embodiment of a process flow 1400 for repositioning and activating a foot pedal system. Representatively, as previously discussed, repositioning may include repositioning a foot pedal assembly (e.g., foot pedal assembly 200, 904 and/or 906) relative to a foot pedal assembly platform (e.g., foot pedal assembly platform 902) from a first position to a second position (block 1402). The first position and the second position could be anywhere on the foot pedal assembly platform. In other words, they are not predetermined, or otherwise predefined, or set positions. In addition, although a first position and a second position are mentioned, any number of positions are possible. Once at the second position, the foot pedal assembly may be locked to the foot pedal assembly platform (block 1404). The assembly may be locked to the platform using any suitable locking mechanism, for example, an electromagnetic mechanism, a suction mechanism, an electrostatic mechanism, a mechanical mechanism, or the like. Process 1400 may further include translating or rotating a foot pedal base of the foot pedal assembly (e.g., foot pedal base 206 of assembly 200) relative to a foot pedal platform of the assembly (e.g., foot pedal platform 202 of assembly 200) from a first activation position to a second activation position (block 1406). Once at the desired activation position, the foot pedal base may be locked to the foot pedal platform at the second activation position (block 1408). To then control the robotic operation or function, the foot pedal can be moved (e.g., pivot) relative to the foot pedal base to an activation position (block 1410). This in turn, sends a control signal to a processor or controller, which actuates the robotic operation or function mapped to the activation position.

Figure 15:
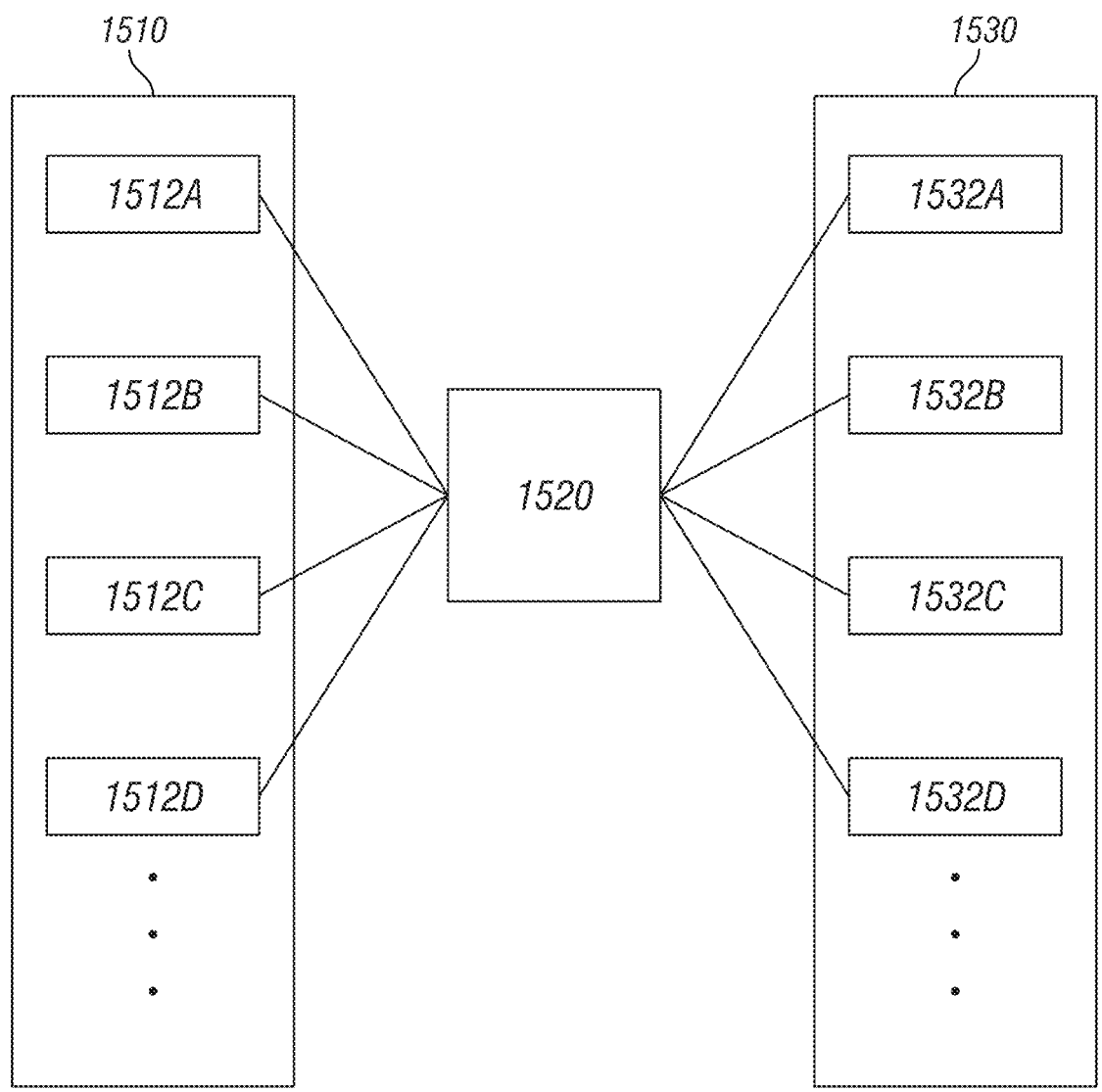
FIG. 15 is a connection diagram schematically depicting exemplary communication between a foot pedal system, a processor/controller, and a robotic surgical system.

FIG. 15 is a connection diagram schematically depicting exemplary communication between a foot pedal assembly or system, a processor/controller, and a robotic surgical system. As shown in FIG. 15, sensor signals from one or more foot pedal assemblies 1510 (e.g., foot pedal assemblies 200, 904, 906) may be communicated to a processor/controller 1520. For example, signals from one or more sensors (1512A, 1512B, 1512C, 1512D, etc.) may indicate a translated and/or pivoted position of the foot pedal in a foot pedal assembly 1510. These sensor signals may be communicated (e.g., via a wired or wireless connection) to the processor/controller 1520. The processor/controller 1520 may generate and communicate control signals (e.g. electrical signals) to control portions of the surgical robotic system 1530. For example, the processor/controller 1520 may generate and communicate control signals to control actuation of a user-selected surgical instrument (e.g., fire and energy pulse, actuate graspers, actuate cutters, control a camera, or activate any suitable surgical instrument 1532A, 1532B, 1532C, 1532D, etc.), engage an instrument clutch mode (e.g., movement of a handheld user interface devices does not move surgical instruments otherwise controlled by user interface devices), select or designate a subset of available robotic arms/instruments for present control, etc. Representatively, the sensors may be sensors configured to detect translated and/or pivoted positions of the foot pedal relative to the foot pedal base, translated and/or pivoted positions of the foot pedal base relative to a foot pedal platform, translated and/or pivoted positions of the foot pedal assembly relative to a foot pedal assembly platform, etc. The sensor signals indicating, for example, current placement of the foot pedal communicated to processor/controller 1520 may also be used to display a graphical representation on a display of the current foot pedal position, such as to inform the user of current position for spatial awareness of the foot pedal, imminent actuation of the foot pedal to an "active" position, a position of the foot pedal base relative to an actuation position, a position of the foot pedal assembly relative to a foot pedal assembly platform, etc.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while the Figures illustrate pedal assemblies and systems for surgical operations, alternative applications may include any application having one or more pedal-actuated functions, which could benefit from the use of a single pedal to control multiple functions, and that is repositionable. Examples include medical devices, aviation, aerospace equipment, aviation equipment, gaming, computer control, music creation, or the like. The description is thus to be regarded as illustrative instead of limiting.

What is claimed is:

1. A foot pedal assembly for controlling a surgical robotic system, the foot pedal assembly comprising:
   a foot pedal base;
   a foot pedal pivotally coupled to the foot pedal base; and
   a foot pedal platform having a contact surface upon which the foot pedal base is positioned, the foot pedal base configured to move across the contact surface relative to a first axis, a second axis and a third axis between an arrangement of activation positions along the contact surface, the first axis and the second axis being parallel to the contact surface, and the third axis being perpendicular to the contact surface, and wherein the foot pedal base translates along the first axis and the second axis and rotates around the third axis.

2. The foot pedal assembly of claim 1 wherein the arrangement of activation positions comprises at least four activation positions located at different corners of the contact surface.

3. The foot pedal assembly of claim 1 wherein each of the activation positions are correlatable to different functions of the surgical robotic system.

4. The foot pedal assembly of claim 1 wherein the contact surface is a planar surface and the foot pedal base is configured to contact and slide across the contact surface along the first axis and the second axis.

5. The foot pedal assembly of claim 1 wherein the first axis is an x-axis and the second axis is a y-axis, and the third axis is a z-axis.

6. The foot pedal assembly of claim 1 wherein the foot pedal is moved relative to the pedal base at any activation position of the arrangement of activation positions to control a corresponding function of the surgical robotic system.

7. The foot pedal assembly of claim 1 wherein the foot pedal comprises a proximal end that is positioned near a heel of a user and a distal end that is positioned near a toe of a user during operation, and the foot pedal is pivotally coupled to an axle positioned closer to the proximal end than the distal end.

8. The foot pedal assembly of claim 1 further comprising a locking assembly operable to lock the foot pedal base at an activation position of the arrangement of activation positions, wherein the locking assembly comprises a first magnet coupled to the foot pedal platform and a second magnet coupled to the foot pedal base.

9. The foot pedal assembly of claim 1 further comprising an active feedback mechanism, the active feedback mechanism operable to output a haptic response to a user.

10. A foot pedal system for controlling a surgical robotic system, the foot pedal system comprising:
a foot pedal assembly operable to control a function of the surgical robotic system, wherein the foot pedal assembly comprises a foot pedal pivotally coupled to a foot pedal base and a foot pedal platform upon which the foot pedal base is slidably coupled; and
a foot pedal assembly platform upon which the foot pedal assembly is positioned, the foot pedal platform is operable to translate and rotate along a surface of the foot pedal assembly platform to any position along the foot pedal assembly platform and control the function of the surgical robotic system at the any position.

11. The foot pedal system of claim 10 further comprising:
a locking assembly operable to selectively engage or disengage the foot pedal assembly platform with the foot pedal assembly at the any position along the foot pedal assembly platform.

12. The foot pedal system of claim 11 wherein the locking assembly comprises an electromagnet assembly operable to selectively engage or disengage the foot pedal assembly with the foot pedal assembly platform, the electromagnet assembly comprising an electromagnet coupled to the foot pedal assembly and a ferromagnetic material coupled to the foot pedal assembly platform.

13. The foot pedal system of claim 11 wherein engaging the foot pedal assembly at the any position prevents movement of the foot pedal assembly with respect to the foot pedal assembly platform until the foot pedal assembly is disengaged.

14. The foot pedal system of claim 10 wherein the foot pedal assembly is operable to translate along an x-axis and a y-axis, and rotate around a z-axis, relative to the foot pedal assembly platform.

15. The foot pedal system of claim 10 wherein the foot pedal assembly is a first foot pedal assembly, the system further comprising a second foot pedal assembly operable to translate or rotate to any position along the foot pedal assembly platform.

16. The foot pedal system of claim 10 further comprising a friction reducing coating at an interface between the foot pedal assembly and the foot pedal assembly platform.

17. A foot pedal system for controlling a surgical robotic system, the foot pedal system comprising:
a foot pedal assembly having a foot pedal base, a foot pedal pivotally coupled to the foot pedal base, and a foot pedal platform, the foot pedal base operable to move relative to the foot pedal platform along an x-axis or a y-axis to an activation position to control a function of the surgical robotic system; and
a foot pedal assembly platform upon which the foot pedal platform of the foot pedal assembly is positioned, the foot pedal platform operable to move relative to, and engage or disengage with, the foot pedal assembly platform at any position along the foot pedal assembly platform,
wherein the foot pedal is operable to pivot around an axle coupled to the foot pedal base, the foot pedal base is operable to rotate with respect to the foot pedal platform around a first axis normal to the axle, and the foot pedal platform is operable to rotate with respect to the foot pedal assembly platform around a second axis normal to the axle.

18. The foot pedal system of claim 17 wherein the foot pedal assembly is operable to be repositioned from a first platform position on the foot pedal assembly platform to a second platform position on the foot pedal assembly platform by a foot of a user, and the foot pedal base is operable to be translated along the foot pedal platform from a first activation position to a second activation position while the foot remains in contact with the foot pedal.

* * * * *